(12) United States Patent
McGrath et al.

(10) Patent No.: US 10,194,791 B2
(45) Date of Patent: Feb. 5, 2019

(54) LARYNGOSCOPE INSERTION SECTION

(71) Applicant: AIRCRAFT MEDICAL LIMITED, Edinburgh (GB)

(72) Inventors: Matthew John Ross McGrath, Edinburgh (GB); Morgan James Walker, Edinburgh (GB)

(73) Assignee: AIRCRAFT MEDICAL LIMITED, Edinburgh (GB)

( * ) Notice: Subject to any disclaimer, the term of this patent is extended or adjusted under 35 U.S.C. 154(b) by 0 days.

(21) Appl. No.: 15/599,116

(22) Filed: May 18, 2017

(65) Prior Publication Data

US 2017/0251916 A1 Sep. 7, 2017

Related U.S. Application Data

(60) Continuation of application No. 14/954,557, filed on Nov. 30, 2015, now Pat. No. 9,662,001, which is a
(Continued)

(30) Foreign Application Priority Data

| Aug. 28, 2007 | (GB) | .................................. | 0716612.7 |
| Aug. 28, 2007 | (GB) | .................................. | 0716613.5 |

(Continued)

(51) Int. Cl.
   *A61B 1/267* (2006.01)
   *A61B 1/00* (2006.01)
   *A61M 16/04* (2006.01)

(52) U.S. Cl.
   CPC .......... *A61B 1/267* (2013.01); *A61B 1/00066* (2013.01); *A61M 16/0488* (2013.01)

(58) Field of Classification Search
   CPC ........................... A61M 16/0488; A61B 1/267
   See application file for complete search history.

(56) References Cited

U.S. PATENT DOCUMENTS

| 2,648,329 A | 8/1953 | Ernst et al. |
| 3,153,267 A | 10/1964 | Rowland et al. |
| (Continued) | | |

FOREIGN PATENT DOCUMENTS

| EP | 284335 | 9/1988 |
| EP | 1598001 | 11/2005 |
| (Continued) | | |

OTHER PUBLICATIONS

*Aircraft Medical v. King S1:10ystems Corp. et al.*, Claim No. CC13P00202, Patents County Court, United Kingdom—Application Notice (Apr. 10, 2013), with Draft Order on Amendment to the Patent and Statement of Reasons (Apr. 10, 2013) and Annexes 1 and 2 (73 pages).

(Continued)

*Primary Examiner* — David Bates
(74) *Attorney, Agent, or Firm* — Fletcher Yoder PC

(57) ABSTRACT

A laryngoscope insertion section comprising a tube guide including at least an inferior tube guiding member and a superior tube guiding member, wherein the thickness of the insertion section in a first region is less than the external diameter of the largest diameter endotracheal tube in an operating range of endotracheal tube sizes plus the thickness of the inferior tube guiding member plus the thickness of the superior tube guiding member. Typically, the insertion section comprises an elongate member and the tube guide is lateral of the elongate member. Typically, an endotracheal tube is retained within the tube guide in flexural tension.

20 Claims, 5 Drawing Sheets

Related U.S. Application Data continuation of application No. 14/073,380, filed on Nov. 6, 2013, now Pat. No. 9,226,651, which is a division of application No. 12/675,916, filed as application No. PCT/GB2008/002900 on Aug. 28, 2008, now abandoned.

(30) Foreign Application Priority Data

| Aug. 28, 2007 | (GB) | 0716615.0 |
|---|---|---|
| Aug. 28, 2007 | (GB) | 0716667.1 |
| Aug. 28, 2007 | (GB) | 0716668.9 |
| Aug. 28, 2007 | (GB) | 0716671.3 |

(56) References Cited

U.S. PATENT DOCUMENTS

| 3,926,196 | A | | 12/1975 | Bornhorst et al. |
| 3,943,920 | A | | 3/1976 | Kandel |
| 4,054,135 | A | | 10/1977 | Berman et al. |
| 4,067,331 | A | * | 1/1978 | Berman ............ A61M 16/0488 128/200.26 |
| 4,211,234 | A | | 7/1980 | Fisher |
| 4,306,547 | A | | 12/1981 | Lowell |
| 4,338,930 | A | | 7/1982 | Williams et al. |
| 4,612,927 | A | | 9/1986 | Kruger |
| 4,832,020 | A | | 5/1989 | Augustine et al. |
| 4,947,896 | A | | 8/1990 | Bartlett et al. |
| 5,024,218 | A | | 6/1991 | Ovassapian et al. |
| 5,038,766 | A | | 8/1991 | Parker et al. |
| 5,042,469 | A | * | 8/1991 | Augustine ......... A61M 16/0488 128/200.26 |
| 5,065,738 | A | | 11/1991 | Van Dam |
| 5,203,320 | A | | 4/1993 | Augustine et al. |
| 5,261,392 | A | | 11/1993 | Wu |
| 5,339,805 | A | | 8/1994 | Parker et al. |
| 5,349,943 | A | | 9/1994 | Ruiz |
| 5,645,519 | A | | 7/1997 | Lee et al. |
| 5,651,761 | A | * | 7/1997 | Upsher ................. A61B 1/267 600/190 |
| 5,702,351 | A | | 12/1997 | Bar Or et al. |
| 5,800,342 | A | * | 9/1998 | Lee ....................... A61B 1/303 600/114 |
| 5,840,013 | A | | 11/1998 | Lee et al. |
| 5,850,832 | A | | 12/1998 | Chu et al. |
| 5,993,383 | A | | 11/1999 | Haase |
| 6,053,166 | A | * | 4/2000 | Gomez ............ A61M 16/0488 128/200.26 |
| 6,142,144 | A | | 11/2000 | Pacey |
| 6,231,505 | B1 | | 5/2001 | Martin |
| 6,471,643 | B1 | | 10/2002 | Henderson |
| 6,655,377 | B2 | | 12/2003 | Pacey |
| 7,182,728 | B2 | | 2/2007 | Cubb et al. |
| 7,946,981 | B1 | | 5/2011 | Cubb |
| 8,079,951 | B2 | | 12/2011 | Yokota |
| 8,202,215 | B2 | | 6/2012 | Xiao et al. |
| 8,479,625 | B2 | | 7/2013 | Klepper |
| 8,814,786 | B2 | | 8/2014 | Young et al. |
| 8,845,525 | B2 | | 9/2014 | McGrath |
| 9,314,151 | B2 | | 4/2016 | McGrath |
| 9,364,140 | B2 | | 6/2016 | McGrath |
| 9,414,743 | B2 | | 8/2016 | McGrath |
| 9,662,001 | B2 | * | 5/2017 | McGrath ................ A61B 1/267 |
| 2002/0068854 | A1 | * | 6/2002 | Heine ..................... A61B 1/07 600/199 |
| 2002/0117171 | A1 | | 8/2002 | Parker |
| 2003/0168059 | A1 | | 9/2003 | Pacey |
| 2005/0090712 | A1 | | 4/2005 | Cubb |
| 2005/0133038 | A1 | | 6/2005 | Rutter |
| 2005/0240081 | A1 | | 10/2005 | Eliachar |
| 2006/0276694 | A1 | | 12/2006 | Acha Gandarias |
| 2007/0106122 | A1 | * | 5/2007 | Yokota ............... A61B 1/00048 600/188 |
| 2008/0185004 | A1 | | 8/2008 | Munn |
| 2009/0032016 | A1 | | 2/2009 | Law et al. |
| 2010/0004514 | A1 | | 1/2010 | Shalman et al. |
| 2010/0256451 | A1 | | 10/2010 | McGrath et al. |
| 2010/0312059 | A1 | | 12/2010 | Mcgrath |
| 2011/0270038 | A1 | | 11/2011 | Jiang et al. |
| 2012/0059223 | A1 | | 3/2012 | McGrath et al. |
| 2012/0095294 | A1 | | 4/2012 | Mcgrath et al. |
| 2012/0095295 | A1 | | 4/2012 | McGrath et al. |
| 2013/0057667 | A1 | | 3/2013 | McGrath |
| 2013/0060089 | A1 | | 3/2013 | McGrath et al. |
| 2013/0060090 | A1 | | 3/2013 | McGrath et al. |
| 2013/0066152 | A1 | | 3/2013 | Chen |
| 2013/0125846 | A1 | | 5/2013 | Kameda et al. |
| 2013/0267780 | A1 | | 10/2013 | Herrmann et al. |
| 2013/0345518 | A1 | | 12/2013 | Law et al. |
| 2014/0121463 | A1 | | 5/2014 | McGrath et al. |
| 2014/0128681 | A1 | | 5/2014 | Fordinal |

FOREIGN PATENT DOCUMENTS

| EP | 1640033 | 3/2006 |
| GB | 2431539 | 4/2007 |
| GB | 2452402 | 3/2009 |
| JP | 64015062 | 1/1989 |
| JP | 2004504919 | 2/2004 |
| JP | 2006518621 | 8/2006 |
| JP | 2006326111 | 12/2006 |
| JP | 2009117116 | 5/2009 |
| WO | 8000538 | 4/1980 |
| WO | 9927840 | 6/1999 |
| WO | 0110293 | 2/2001 |
| WO | 211608 | 2/2002 |
| WO | 2004008951 | 1/2004 |
| WO | 2004073510 | 9/2004 |
| WO | 2005107575 | 11/2005 |
| WO | 2007070944 | 6/2007 |

OTHER PUBLICATIONS

*Aircraft Medical v. King Systems Corp. et al.*, Claim No. CC13P00202, Patents County Court, United Kingdom—Defense and Counterclaim (Mar. 14, 2013), with Annexes 1-9 (111 pages).

*Aircraft Medical v. King Systems Corp. et al.*, Claim No. CC13P00202, Patents County Court, United Kingdom—Letter from UKIPO dated Jun. 4, 2013, re Application for Amendment (3 pages).

*Aircraft Medical v. King Systems Corp. et al.*, Claim No. CC13P00202, Patents County Court, United Kingdom—Reply and Defence to Counterclaim (Apr. 10, 2013), with Annexes E-1 (31 pages).

*Aircraft Medical v. King Systems Corp. et al.*, Claim No. CC13P00202, Patents County Court, United Kingdom—Reply to Defence to Counterclaim and Notice of Opposition to Proposed Amendments (May 15, 2013) and Annexes 10-13 (49 pages).

*Aircraft Medical v. King Systems Corp. et al.*, Claim No. CC13P000202, Patents County Court, United Kingdom—Revised Annex B to the Particulars of Infringement (8 pages).

*Aircraft Medical v. King Systems Corp. et al.*, Claim No. CC13P00202, Patents County Court, United Kingdom, Initial pleadings of the case: Jan. 15, 2013 Claim Form, Particulars of Claim, Particulars of Infringement with Annexes A-D (72 pages).

Apr. 5, 2013 Examination Report (with English translation) for Japanese Application No. 2010-522435.

Apr. 5, 2013 Japanese Examination Report (with English translation) for Japanese Application No. 2010-522434.

Apr. 9, 2013 Notice of Grounds of Rejection for Japanese Application No. 2010-522435.

Benumof'S Airway Management: Principles and Practice, 2d Ed., Edited by Carin A. Hagberg, MD, Mosby Elservier, 2007, pp. 559-560.

C.H. Maharaj et al., "Evaluation of intubation using the Airtraq or Macintosh laryngoscope by anaesthetists in easy and simulated difficult laryngoscopy—manikin study," Anaesthesia, 2006, 61, pp. 469-477.

C.H. Maharaj et al., "Learning and performance of tracheal intubation by novice personnel: a comparison of the Airtraq and Macintosh laryngoscope," Anaesthesia, 2006, 61, pp. 671-677.

(56) References Cited

OTHER PUBLICATIONS

Dec. 12, 2008 International Search Report for International Application No. PCT/GB2008/002903.
Dec. 20, 2007 UK Search Report for UK Application No. GB0716613.5.
Dec. 20, 2007 UK Search Report for UK Application No. GC0716668.9.
Dec. 28, 2007 UK Search Report for UK Application No. GC0716671.3.
Jan. 22, 2013 Japanese Examination Report (with English translation) for Japanese Application No. 2010-522435.
Jun. 27, 2008 UK Search Report for UK Application No. GB0716612.7.
Jun. 27, 2008 UK Search Report for UK Application No. GB0716615.0.
Jun. 27, 2008 UK Search Report for UK Application No. GB0716667.1.
May 14, 2009 International Search Report for PCT/GB2008/002900.
May 6, 2013 Office Action issued in U.S. Appl. No. 12/675,892.
May 6, 2015 Office Action issued in U.S. Appl. No. 12/675,892.
Mercury Medical Brochure, "Introducing . . . The CookGas ILA—Intubating Laryngeal Airway and Removal Stylet," Jun. 2006, pp. 1-41.
Nov. 19, 2008 UK Search Report for UK Application No. GB0815656.4.
Nov. 19, 2008 UK Search Report for UK Application No. GB0815658.0.
Nov. 19, 2008 UK Search Report for UK Application No. GB0815659.8.
Nov. 19, 2008 UK Search Report for UK Application No. GB0815660.6.
Nov. 19, 2008 UK Search Report for UK Application No. GB0815661.4.
Nov. 19, 2008 UK Search Report for UK Application No. GB0815662.2.
Nov. 19, 2008 UK Search Report for UK Application No. GB0815663.0.
Sep. 13, 2012 Office Action issued in U.S. Appl. No. 12/675,892.
Sep. 5, 2014 Office Action issued in U.S. Appl. No. 12/675,892.

\* cited by examiner

LARYNGOSCOPE INSERTION SECTION

RELATED APPLICATIONS

This application is a continuation of U.S. patent application Ser. No. 14/954,557 filed Nov. 30, 2015, which is a continuation of U.S. patent application Ser. No. 14/073,380, filed Nov. 6, 2013, which is a divisional of U.S. patent application Ser. No. 12/675,916, filed Jun. 7, 2010, which is the U.S. National Phase of International Application No. PCT/GB2008/002900, filed Aug. 28, 2008, which designated the U.S. and claims priority to Great Britain Application Nos. 0716671.3, filed Aug. 28, 2007, 0716612.7, filed Aug. 28, 2007, 0716613.5, filed Aug. 28, 2007, 0716615.0, filed Aug. 28, 2007, 0716667.1, filed Aug. 28, 2007, and 0716668.9, filed Aug. 28, 2007, the entire contents of each of which are hereby incorporated by reference.

FIELD OF THE INVENTION

The invention relates to the field of laryngoscope insertion sections which include a tube guide for detachably retaining an endotracheal tube and guiding a retained endotracheal tube towards a patient's larynx.

BACKGROUND TO THE INVENTION

Laryngoscopes comprise insertion sections, which are the elongate part of a laryngoscope which extends towards and into a patient's oral cavity during intubation. Insertion sections may be removably attachable to a laryngoscope body, integral parts of laryngoscopes or themselves function as laryngoscopes. As well as an insertion section, laryngoscopes typically comprises a handle which is usually elongate and which may be arranged at an angle to the proximal end of the insertion section or generally parallel to the proximal end of the insertion section, or at any angle therebetween.

Some known laryngoscope insertion sections, such as Miller or Wisconsin insertion sections, are substantially flat. However, the insertion section of a laryngoscope is more commonly bent to better enter through a patient's oropharynx towards their larynx. Some known insertion sections include first and second straight portions, with a bend therebetween, or are curved, at least in part. Within this specification and the appended claims, the inferior surface is the surface of an insertion section which faces the patient's tongue in use.

The opposite surface is referred to as the superior surface. Words such as inferior, inferiorly, superior and superiorly are used in corresponding senses. A superior-inferior axis is a virtual axis extending parallel to the superior and inferior directions.

The words distal and distally refer to being towards the end of the insertion section which extends towards a patient's trachea in use and the words proximal and proximally refer to being towards the person carrying out intubation in use.

It is known to provide a laryngoscope insertion section including a tube guide which extends along the length of the insertion section. For example, WO 04/073510 (Gandarias) discloses a laryngoscope insertion section including a tube guide which extends laterally from an elongate member which contains apparatus to provide an image of a patient's larynx in use. The tube guide has inferior and superior walls which extend continuously along the length of the tube guide. An endotracheal tube may be fitted into the tube guide and the insertion of the endotracheal tube into a patient's larynx can be viewed by a user. The endotracheal tube can then be detached from the insertion section whilst the insertion section remains within a patient and the insertion section can be removed, leaving the endotracheal tube in place.

Tube guides can facilitate intubation by ensuring that, once an insertion section is in place and the patient's larynx sighted, an endotracheal tube is already in the correct location to be pushed forward and inserted into a patient's larynx. However, a potential disadvantage is that tube guides increase the bulk of the insertion section. Accordingly, the present invention aims to provide an insertion section with a tube guide in which the insertion section is adapted to reduce its bulk, to facilitate introduction of the insertion section into a patient with an endotracheal tube in place within the tube guide.

Another problem with known insertion sections with tube guides is that they are typically designed for use with endotracheal tubes of a limited range of sizes. Some aspects of the present invention are directed to providing insertion sections adapted to guide a wider operating range of endotracheal tube sizes than known insertion sections with tube guides.

Furthermore, the laryngoscope disclosed in WO 04/073510 has a generally J-shaped insertion section which retains an endotracheal tube in a generally J-shaped configuration. This has two significant disadvantages. Firstly, the insertion of a J-shaped insertion section into a patient's oral cavity can be difficult. A J-shaped insertion section must be tilted backwards and forwards during insertion to insert the distal end, manipulate the patient's anatomy and obtain a good view of the patient's larynx. It is preferable to provide a laryngoscope which can be more readily inserted. Secondly, this arrangement means that, when the endotracheal tube is pushed forward to advance the tube, a resistive force is developed on the superior side of the tube guide where the endotracheal tube bends from being substantially straight to curved, which increases friction. Some embodiments of the present invention aim to provide an insertion section which is easier to insert into a patient and/or which has a tube guide along which an endotracheal tube can be more readily advanced.

Some aspects of the present invention aim to provide an insertion section having a tube guide which is easier to operate, for example because less force is required, than with known insertion sections with tube guides, or to provide improved adjustability.

SUMMARY OF THE INVENTION

According to a first aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx, the tube guide comprising a plurality of tube guiding members having tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and a first superior tube guiding member having a tube guiding surface on an inferior side thereof for contacting and thereby guiding the superior surface of a retained endotracheal tube, wherein the insertion section comprises a first region, which is proximal of the tube guiding surface of the first superior tube guiding member, where the thickness of the insertion section is less than the sum of the external diameter of the largest external diameter endotracheal tube in an operating range of endotracheal tube sizes plus the mean thickness of the inferior tube guiding member plus the mean thickness of the first superior tube guiding member.

Accordingly, at least in the first region, the insertion section is narrower than would be the case if it had tube guiding walls which extended both inferiorly and superiorly of a retained endotracheal tube in use, which walls ran continuously along the length of the insertion section.

By the thickness of an insertion section, we refer to width or the displacement, parallel to a superior-inferior axis, from the most inferior point on the inferior side of the insertion section to the most superior point on the superior side of the insertion section, through a given cross-section orthogonal to the length of the insertion section. Words such as "thick", "thicker", "narrow", and "narrower" should be construed accordingly.

By the mean thickness of a tube guiding member we refer to the mean distance from the inferior side to the superior side where the tube guiding surface of the tube guiding member is most inferior or most superior, as appropriate, along the length of the tube guiding surface of the tube guiding member. We do not intend that the thickness of any parts of tube guiding members which do not contact and thereby guide the inferior or superior surface of retained endotracheal tubes are taken into account when assessing the mean thickness of a tube guiding member as any such part is not subject to the same strength requirements as the parts which contact and thereby guide the inferior or superior surface of retained endotracheal tubes and it is these strength requirements which typically determine the minimum thickness of a tube guiding member. The tube guiding surfaces of the or each superior tube guiding member may extend along the length of, or along part of the length of, the or each superior tube guiding member. The tube guiding surface of the inferior tube guiding member may extend along the length of, or part of the length of, the inferior tube guiding member.

Preferably, the insertion section is configured such that, in the first region, the combined thickness of the insertion section and a retained endotracheal tube having the largest external diameter in the operating range of endotracheal tube sizes, is less than the sum of the external diameter of the largest external diameter endotracheal tube in the operating range of endotracheal tube sizes plus the mean thickness of the inferior tube guiding member plus the mean thickness of the first superior tube guiding member.

At least a part of, and optionally all of, the tube guiding surface of the first superior tube guiding member may be opposite at least a part of the tube guiding surface of the inferior tube guiding member. Alternatively, the tube guiding surface of the first superior tube guiding member and the tube guiding surface of the inferior tube guiding member may not be opposite each other.

By providing an elongate laryngoscope insertion section having a first region which has a thickness that is less than the sum of the external diameter of the largest external diameter endotracheal tube in an operating range of endotracheal tube sizes plus the mean thickness of the inferior tube guiding member plus the mean thickness of the first superior tube guiding member, the insertion section is narrower at the first region in use than would be the case if tube guiding members of the same thickness as the inferior and first superior tube guiding members were provided in the first region and spaced apart sufficiently to receive an endotracheal tube having the largest external diameter in an operating range of endotracheal tubes.

By the external diameter of the largest external diameter endotracheal tube in an operating range of endotracheal tube sizes, we refer to the external diameter of the largest external diameter endotracheal tubes with which the insertion section can be reliably used. This will depend on the scale of the insertion section which will itself depend on the application of the insertion section. An insertion section for use with adult humans may, for example, be adapted to be usable reliably with endotracheal tubes with an external diameter of up to 12.3 mm. Tubes of this external diameter are referred to as Size 9.0 in the field. The minimum external diameter may be around 5.5 mm. Where the insertion section is made from a plastics material, the mean thickness of the inferior and first superior tube guiding members typically requires to be at least 0.75 mm (preferably around 1.5 mm) to provide suitable mechanical strength for internal use. Accordingly, the thickness of the first region is preferably less than 15.3 mm, more preferably less than 14.6 mm, 13.8 mm or more preferably less than 13.1 mm, in the case of an insertion section for inserting endotracheal tubes into adult humans.

The dimensions of an insertion section for use with infant humans, including new born infants, are typically scaled proportionately from the dimensions of an insertion section for use with human adults. Nevertheless, the proportions of some features, such as the thickness of the tube guiding members, may not scale proportionately. In the case of an insertion section for inserting endotracheal tubes into infant humans, including new born infants, the operating range of external tube diameters may be 1.0 to 5.0 mm, and the thickness of the first region is preferably less than 8.0 mm, preferably less than 7.0 mm, or more preferably less than 6.0 mm.

The thickness of the insertion section at the first region may be less than the external diameter of the largest diameter endotracheal tube in the operating range of endotracheal tube sizes.

The first region may extend from the proximal end of the insertion section to the proximal end of the tube guiding surface of the first superior tube contacting member. The first region may extend from the proximal end of the insertion section to the proximal end of the first superior tube contacting member. The first region may include part of the proximal half of the insertion section but not extend to the proximal end of the insertion section. The first region preferably comprises a region of the insertion section which is close to a patient's teeth when the insertion section is fully inserted into a patient, as this can reduce the risk of damage to a patient's teeth.

The insertion section is typically curved such that at least a portion of the superior surface is excurvate and at least a portion of the inferior surface is incurvate. The first superior tube guiding member is typically provided towards the distal end of the insertion section. Preferably, the first superior tube guiding member is provided close to, but not at, the distal end of the insertion section. Typically, the first superior tube guiding member guides a retained endotracheal tube towards a patient's larynx. Typically, the tube guiding surface of the first superior tube guiding member and the tube guiding surface of the inferior tube guiding member together guide a retained endotracheal tube towards a patient's trachea in use.

Typically, the tube guiding surface of the first superior tube guiding member is the most distal location where the insertion section contacts the superior surface of a retained endotracheal tube. Typically, the tube guiding surface of the inferior tube guiding member is the most distal location where the insertion section contacts the inferior surface of a retained endotracheal tube for endotracheal tubes of a range of external diameters (typically at the upper end of the operating range of endotracheal tube sizes). The insertion section may be configured such that endotracheal tubes at the lower end of the operating range of endotracheal tube sizes do not contact the inferior tube guiding member opposite the first superior tube guiding member but endotracheal tubes at the upper end of the operating range of endotracheal tube sizes do contact the inferior tube guiding member opposite the first superior tube guiding member.

Preferably, the tube guide is arranged to guide a retained endotracheal tube such that the inferior surface of a retained endotracheal tube is inferior of the superior surface of the insertion section and the superior surface of a retained endotracheal tube is superior of the inferior surface of a retained endotracheal tube at least in the first region and typically from where the insertion section extends between a patient's teeth in use and the first superior tube guiding member. This arrangement fits better with the general shape of the oral cavity than devices where the endotracheal tube is retained entirely inferiorly or entirely superiorly of the insertion section at a corresponding region.

The insertion section typically comprises a curved portion (for example, the insertion section may be entirely curved) such that the inferior surface of the insertion section is incurvate and the superior surface of the insertion section is excurvate. The first superior tube guiding member is located sufficient distally of the first region to guide a retained tube at an angle of at least 20°, and preferably at least 30° to the angle at which a retained tube is guided in the first region. The first superior tube guiding member is preferably arranged to guide an endotracheal tube towards a patient's larynx when the insertion section is fully inserted in use.

The first region of the insertion section which has a thickness which is less than the sum of the external diameter of the largest external diameter endotracheal tube in an operating range of endotracheal tube sizes plus the mean thickness of the inferior tube guiding member plus the mean thickness of the first superior tube guiding member preferably extends along at least 1 cm of the length of the insertion section. More preferably, the first region extends along at least 1.5 cm, and more preferably at least 2.5 cm, of the length of the insertion section which is close to a patient's teeth in use, to provide a user with an insertion section which is relatively thin along a significant length of the insertion section to increase manoeuvrability and reduce the risk of damage to a patient's teeth.

The plurality of tube guiding members may further comprise a second superior tube guiding member having a tube guiding surface on an inferior side thereof for contacting and thereby guiding the superior surface of a retained endotracheal tube, wherein the second superior tube guiding member is proximal of the first superior tube guiding member and the tube guiding surfaces of the first and second superior tube guiding members are spaced apart. Thus, the superior surface of a retained endotracheal tube will typically be exposed between the first and second superior tube guiding members.

In an insertion section for the intubation of human adults, the tube guiding surfaces of the first and second superior tube guiding members are typically spaced apart by at least 2 cm, more preferably at least 4 cm and most preferably at least 6 cm. When the insertion section is curved, the direction of the insertion section at the first superior tube guiding member typically differs by at least 20° and preferably at least 30° from the direction of the insertion section at the second superior tube guiding member.

Preferably, the first superior tube guiding member is located towards, but not at, the distal end of the insertion section.

The second superior tube guiding member may be arranged to be located close to the teeth of a patient of typical dimensions when the insertion section is fully inserted into a patient. The first region may comprise some or all of the second superior tube guiding member. The second superior tube guiding member may be located proximal of the teeth of a patient of typical dimensions when the insertion section is fully inserted into a patient such that it would not pass into the oral cavity of a patient of typical dimensions in use.

Preferably, the insertion section is arranged to leave the inferior surface of a retained endotracheal tube exposed opposite the second superior tube guiding member. Typically, no inferior tube guiding member is provided opposite the second superior tube guiding member.

Preferably, the insertion section is arranged to leave the superior surface of a retained endotracheal tube exposed opposite at least the proximal end of and optionally all of the inferior tube guiding member. It may be that no superior tube guiding member is provided opposite at least the proximal end of and optionally all of the inferior tube guiding member.

Thus, at least a region of the insertion section close to a patient's teeth in use is narrower than would be the case if an inferior tube guiding member was provided opposite the second superior tube guiding member and spaced apart from the second tube guiding member so as to leave a gap therebetween with a thickness at least equal to the external diameter of the largest endotracheal tube in an operating range of endotracheal tubes. Preferably, the distal end of the tube guiding surface of the second superior tube guiding member and the proximal end of the tube guiding surface of the inferior tube guiding member are spaced apart along the length of the insertion section, preferably by at least 0.5 cm, more preferably by at least 1 cm and most preferably by at least 2 cm. Preferably also, the distal end of the second tube guiding member and the proximal end of the inferior tube guiding member are spaced apart along the length of the insertion section, preferably by at least 0.5 cm, preferably by at least 1 cm and most preferably by at least 2 cm.

Preferably, the component which is parallel to a superior-inferior axis of the displacement between the distal end of the tube guiding surface of the second superior tube guiding member and the proximal end of the tube guiding surface of the inferior tube guiding member is less than the external diameter of the largest external diameter endotracheal tube in an operating range of endotracheal tube sizes. Preferably also, the distance between the distal end of the second tube guiding member and the inferior tube guiding member, parallel to a superior-inferior axis, is less than the external diameter of the largest external diameter endotracheal tube in an operating range of endotracheal tube sizes.

Thus, the tube guide may be arranged to receive an endotracheal tube other than parallel to the length of the insertion section, for example, the tube guide may be arranged to receive an endotracheal tube such that it extends distally and superiorly between the proximal end of the tube guiding surface of the inferior tube guiding member and the distal end of the tube guiding surface of the second superior tube guiding member. Preferably, the thickness of the insertion section between the second superior tube guiding member and the first tube guiding member is less than the thickness of the insertion section at one and preferably both of the first and second superior tube guiding members.

Preferably, the tube guide is arranged such that, for endotracheal tubes of a range of external diameters (typically including endotracheal tubes having the largest external diameter in an operating range of endotracheal tube sizes) a retained endotracheal tube will not be retained parallel to the length of the insertion section but have a different radius of curvature to the insertion section along at least a portion of the insertion section (typically from the most proximal location where the insertion section contacts the superior surface of a retained endotracheal tube to the most distal location where the insertion section contacts the superior surface of a retained endotracheal tube). The tube guide may be arranged such that endotracheal tubes having an external diameter at the top end of the operating range of endotracheal tube sizes are retained with a smaller radius of curvature than the insertion section along at least a portion of the insertion section (typically from the most proximal location where the insertion section contacts the superior surface of a retained endotracheal tube to the most distal location where the insertion section contacts the superior surface of a retained endotracheal tube). The tube guide may be arranged such that endotracheal tubes having an external diameter at the bottom end of the operating range of endotracheal tube sizes are retained with a higher radius of curvature than the insertion section along at least a portion of the insertion section (typically from the most proximal location where the insertion section contacts the superior surface of a retained endotracheal tube to the most distal location where the insertion section contacts the superior surface of a retained endotracheal tube).

In particular, the plurality of tube guiding members may comprise a second superior tube guiding member having a tube guiding surface which is spaced apart from the tube guiding surface of the first superior tube guiding member and arranged such that, for endotracheal tubes of a range of external diameters (typically including endotracheal tubes having the largest external diameter in an operating range of endotracheal tube sizes), a retained endotracheal tube will not be retained parallel to the length of the insertion section between the first and second superior tube guiding members.

The tube guide may be arranged such that, for at least some endotracheal tubes with an external diameter within an operating range of external diameters, the superior surface of a said retained endotracheal tube extends superiorly of the superior surface of the insertion section (typically the superior surface of the elongate member, where provided), along at least a portion of the length of the insertion section, towards the middle of the insertion section. Typically, the tube guide is arranged such that, for at least some endotracheal tubes with an external diameter within an operating range of external diameters, the superior surface of retained said endotracheal tube extends superiorly of the superior surface of the insertion section at at least one location between the first and second superior tube guiding members, where provided.

Preferably, the tube guiding members are arranged such that, for endotracheal tubes having a range of external diameters within the operating range of endotracheal tube external diameters (typically at the upper end of the operating range of endotracheal tube external diameters) a retained endotracheal tube will typically contact the tube guiding surface of either one of or preferably both the proximal and distal superior tube guiding members only at the distal ends of the respective tube guiding member, when a retained endotracheal tube is at rest, retained within the tube guide. Endotracheal tubes having a range of external diameters within the operating range of endotracheal tube external diameters (typically at the upper end of the operating range of endotracheal tube external diameters) may only contact the tube guiding surface of the inferior tube guiding member at the proximal end of the tube guiding surface, when a retained endotracheal tube is at rest, retained within the tube guide. This arrangement reduces friction when the endotracheal tube is subsequently advanced towards a patient's larynx.

Preferably, the tube guide is arranged to retain an endotracheal tube under flexural tension from the most proximal location where the tube guide contacts the superior surface of a retained endotracheal tube to the most distal location where the tube guide contacts the superior surface of a retained endotracheal tube. This facilitates retention of the endotracheal tube within the tube guide. Preferably, the tube guide also contacts the inferior surface of a retained endotracheal tube intermediate the most proximal and most distal locations where the tube guide contacts the superior surface of a retained endotracheal tube, such that a retained endotracheal tube exerts a superior force on the tube guide at the most proximal and most distal locations where the tube guide contacts the superior surface of a retained endotracheal tube and an inferior force at the said location where the tube guide contacts the inferior surface of a retained endotracheal tube. The use of at least three points of contact facilitates grip. The retention of an endotracheal tube under flexural tension is of particular benefit where the tube guide opens laterally as the flexural tension increases the friction which opposes lateral movement of the retained endotracheal tube. Nevertheless, the use of only three points of contact reduces friction when the endotracheal tube is advance longitudinally compared to an arrangement in which a retained endotracheal tube is in contact with a guide wall along a substantial portion of the tube guide.

The tube guiding surface of the first superior tube guiding member may extend distally and inferiorly (i.e. such that it extends inferiorly towards the distal end) at an angle to the insertion section. Similarly, the second superior tube guiding member, where present, may extend distally and superiorly (i.e. such that it extends superiorly towards the distal end). This facilitates the retention of an endotracheal tube in a curved configuration, under flexural tension.

The tube guide may be arranged such that, for endotracheal tubes of a range of external diameters (typically including endotracheal tubes having the largest external diameter in an operating range of endotracheal tube sizes), a retained endotracheal tube is continuously curved from where it extends into a patient's mouth when it is fully inserted in use to the first superior tube guiding member. Where a second superior tube guiding member is provided, the tube guide may be arranged such that, for endotracheal tubes of a range of external diameters (typically including endotracheal tubes having the largest external diameter in an operating range of endotracheal tube sizes), a retained endotracheal tube is continuously curved from the second superior tube guiding member to the first superior tube guiding member.

The curvature may or may not be constant.

Where the tube guiding surfaces of the first and second superior tube guiding members are spaced apart such that the superior surface of a retained endotracheal tube is exposed between the first and second superior tube guiding members, and the tube guide is arranged so that for endotracheal tubes of a range of external diameters (typically including endotracheal tubes having the largest external diameter in an operating range of endotracheal tube sizes), said retained endotracheal tubes are continuously curved from where they extend into a patient's mouth when the insertion section is fully inserted in use to the first superior tube guiding member, this enables the insertion section and tube guide to be used with endotracheal tubes of a wider range of diameters than would be the case for a tube guide defined by continuous inferior and superior tube guiding surfaces. Preferably, the insertion section only includes one or more tube guiding surfaces which extend to contact and thereby guide the inferior surface of a retained endotracheal tube distally of a patient's teeth when the insertion section is fully inserted into a patient. Accordingly, the tube guide preferably only covers the inferior surface of a retained endotracheal tube distally of a patient's teeth when the insertion section is fully inserted into a patient.

The tube guiding surface of the inferior tube guiding member preferably extends proximally of the tube guiding surface of the first superior tube guiding member. Thus, the inferior surface of a retained endotracheal tube may be guided proximally of the first superior tube guiding member without the superior surface of a retained endotracheal tube being guided along the entire length of the tube guiding surface of the inferior tube guiding member. This reduces the overall bulk of the insertion section as a retained tube can be guided adequately using a first superior tube guiding member with only a relatively short tube guiding surface and an inferior tube guiding member with a tube guiding surface which extends distally of the tube guiding surface of the first superior tube guiding member. Preferably, the tube guiding surface of the inferior tube guiding member extends at least 1 cm, preferably at least 2 cm and most preferably 4 to 5 cm proximally of the tube guiding surface of the first superior tube guiding member. The tube guiding surface of the inferior tube guiding member may be entirely proximal of the tube guiding surface of the first superior tube guiding member, further reducing bulk.

Preferably, the tube guide is arranged such that a retained endotracheal tube can be removed laterally from the tube guide. This facilitates removal of the endotracheal tube in situ within a patient. Preferably, the insertion section is arranged such that a retained endotracheal tube remains exposed along an entire lateral side (e.g. along the entirety of the most lateral point on the tube, along the length of the tube). By avoiding covering the lateral side of a retained endotracheal tube, the overall bulk of the insertion section is reduced.

Preferably, the insertion section comprises an elongate member which extends along the majority of the length of the insertion section, with the tube guide arranged to retain an endotracheal tube laterally of the elongate member. The tube guiding members preferably extend laterally of, and typically from, the elongate member. The elongate member may comprise imaging apparatus, such as an imaging device (e.g. a camera) or image conduction apparatus (such as one or more fibre optic cables or one or more reflective surfaces) for imaging a patient's laryngeal area in use. The elongate member may comprise illumination apparatus, such as a light source, including a bulb or one or more fibre optical cables through which light may be conducted, for illuminating a patient's laryngopharynx in use. The elongate member may conduct one or more cable therein, such as electrical wires which relay signals from an imaging device and/or provide power to an imaging device and/or light source, where present.

The elongate member may define a bore therein, which typically extends from the proximal end of the elongate member, which may be a through-bore which is open at both ends or which may be enclosed at a distal end of the bore. The bore may be configured to receive imaging apparatus and/or illumination apparatus. The bore may be configured to receive an elongate insertion section supporting member which resists flexing of the insertion section. The bore may be configured to receive an elongate insertion section supporting member which comprises imaging apparatus and/or illumination apparatus. Where the bore is enclosed at a distal end, the elongate member is preferably liquid tight to prevent contamination of imaging apparatus and/or illumination apparatus enclosed therein.

Preferably, at at least one location where the insertion section comprises a said elongate member with an adjacent tube guide, the elongate member and tube guide are configured such that the thickness of the elongate member is less than the thickness of the adjacent tube guide plus the external diameter of a retained endotracheal tube having the largest external diameter in the operating range of endotracheal tube sizes. The said location may be adjacent to the first superior tube guiding member. The said location may be adjacent to the inferior tube guiding member. The said location may be adjacent to the second superior tube guiding member, where provided.

Accordingly, by providing an elongate member which is narrower than the adjacent tube guide, we provide an insertion section which is less bulky than would be the case if the elongate member was the same thickness as the tube guide.

Preferably, at at least one location where the tube guide comprises a superior tube guiding member, such as the first superior tube guiding member, or a further tube guiding member which is proximal of the first superior tube guiding member, where provided, the superior tube guiding member extends further in a superior direction than the elongate member, adjacent to the superior tube guiding member.

Preferably, at at least one location where the tube guide comprises an inferior tube guiding member, the inferior tube guiding member extends further in an inferior direction than the elongate member, adjacent to the inferior tube guiding member.

Accordingly, by providing a superior tube guiding member which extends further in a superior direction than the adjacent elongate member and/or an inferior tube guiding member which extends further in a superior direction than the adjacent elongate member, a less bulky insertion section with a lateral tube guide is provided than would be the case if the superior tube guiding member did not extend further in a superior direction than the adjacent elongate member and/or the inferior tube guiding member did not extend further in an inferior direction than the adjacent elongate member.

Preferably, where the insertion section comprises an elongate member with an adjacent tube guide arranged to retain an endotracheal tube laterally of the elongate member, there is at least one location, proximal of the first superior tube guiding member, where an endotracheal tube is retained in use laterally of the elongate member with the inferior and superior sides of the endotracheal tube being left exposed. Preferably, no tube guiding member is provided at the location. Where first and second superior tube guiding members are provided, the said location is typically intermediate the first and second superior tube guiding members.

In the first region, or a portion of the first region, a retained endotracheal tube at the upper end of the operating range of endotracheal tube sizes may have both its inferior and superior surfaces left exposed in use and extend inferiorly and superiorly of an adjacent section of elongate member. Thus, in the first region, or a portion of the first region, the thickness of the insertion section may be less than three-quarters, or preferably less than half of the external diameter of the largest external diameter endotracheal tube in an operating range of endotracheal tube sizes.

Preferably, the first superior tube guiding member extends laterally and superiorly from the elongate member, from the superior surface of the elongate member or from the lateral edge of the elongate member intermediate the inferior and superior surfaces of the elongate member. Where a second superior tube guiding member is provided, the second superior tube guiding member preferably extends laterally and superiorly from the elongate member, from the superior surface of the elongate member or from the lateral edge of the elongate member intermediate the inferior and superior surfaces of the elongate member.

The first superior tube guiding member and/or second superior tube guiding member, where present, typically comprises a lateral portion which is arranged to extend distally and inferiorly beyond the midline of a retained endotracheal tube. Thus, the tube guiding surface of the first superior tube guiding member (and second superior tube guiding member when present) is typically incurvate.

Preferably, the inferior tube guiding member extends laterally and inferiorly from the elongate member. The inferior tube guiding member typically comprises a lateral portion which is arranged to extend distally and superiorly beyond the midline of a retained endotracheal tube. This, the tube guiding surface of the inferior tube guiding member is typically incurvate.

Preferably, the lateral extent of the tube guiding members from the elongate member exceeds at least 50%, more preferably at least 60%, or more preferably at least 70% of the diameter of the largest endotracheal tubes in an operating range of endotracheal tube sizes in order to extend past the midline of and thereby guide endotracheal tubes. For example, where the operating range of endotracheal tube sizes extends up to 12.3 mm, the tube guiding members preferably extend at least 6.1 mm (more preferably at least 7.3 mm and most preferably at least 8.5 mm) laterally from the elongate member. Where the operating range of endotracheal tube sizes extends up to 5.0 mm, the tube guiding members preferably extend at least 2.5 mm laterally from the elongate member.

The inferior tube guiding member is preferably continuous but may alternatively be discontinuous. Where an elongate member is present, the inferior tube guiding member typically extends from, or from near, the inferior side of the elongate member. The inferior surface of the tube guiding member may be level with the inferior side of the tube guide. The inferior tube guiding member may extend to the distal end of the insertion section.

The first superior tube guiding member may comprise two or more separate portions or be continuous. Where present, the second superior tube guiding member may comprise two or more separate portions or be continuous.

Preferably, the insertion section is arranged so that an intubater can contact an endotracheal tube retained by the tube guide within a patient's mouth, in use. This increases the amount of control which is available to the intubater and may be preferred by intubaters who have been trained to carry out intubation using traditional laryngoscopes, who are used to being able to manipulate the endotracheal tube within the patient's mouth. Where the insertion section comprises a second superior tube guiding member having a tube guiding surface which is spaced apart from the tube guiding surface of the first superior tube guiding member, the insertion section may be arranged so that an intubater can contact an endotracheal tube distally of the tube guiding surface of the section superior tube guiding member. The insertion section may be arranged to that an intubater can contact one or more of the inferior or superior surfaces of an endotracheal tube retained within the tube guide within a patient's mouth, in use (e.g. distally of the distally of the tube guiding surface of the second superior tube guiding member, where present). The insertion section may be arranged to that an intubater can contact a lateral surface of an endotracheal tube retained within the tube guide within a patient's mouth, in use (e.g. distally of the distally of the tube guiding surface of the second superior tube guiding member, where present). The insertion section may be arranged so that an intubater can contact opposite inferior and superior surfaces of the endotracheal tube within a patient's mouth, in use, (e.g. distally of the distally of the tube guiding surface of the second superior tube guiding member, where present), to facilitate grip and enable them to gently pinch the tube.

Preferably, the insertion section is rigid. Preferably, at least part of the insertion section is transparent. The insertion section may be made from a plastics material. The insertion section may be moulded from a plastics material. The insertion section may be monolithic. Where the insertion section comprises an elongate member having a bore, the insertion section may function to protect optical apparatus within the bore in use. Accordingly, the insertion section may be disposable.

The insertion section may be an integral part of a laryngoscope, which may comprise a handle. The insertion section may be removably attachable to a laryngoscope, body, which may comprise a handle. The insertion section may function as a laryngoscope. Preferably, the insertion section is of suitable size for use in the intubation of adults. Preferably, the operating range of endotracheal tube sizes includes endotracheal tubes having an external diameter of 12.3 mm. The relevance of this size is that this is the external diameter of what is generally referred to in the industry as Size 9.0 endotracheal tubes, being one of the largest sizes in common use. However, tubes of this size are sufficiently broad to present an engineering challenge if an insertion section is to be provided with an integral tube guide which capable of operating reliably with tubes of these size but does not present an obstruction.

According to a second aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx, the tube guide comprising a plurality of tube guiding members having tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and first and second superior tube guiding members each of which has a tube guiding surface on an inferior side thereof for contacting and thereby guiding the superior surface of a retained endotracheal tube, wherein the second superior tube guiding member is proximal of the first superior tube guiding member and the tube guiding surfaces of the first and second superior tube guiding members are spaced apart, wherein the tube guide is arranged to leave exposed the inferior surface of a retained endotracheal tube opposite the tube guiding surface of the second superior tube guiding member.

According to a third aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx, the tube guide comprising a plurality of tube guiding members having tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and a first superior tube guiding member having a tube guiding surface on an inferior side thereof for contacting and thereby guiding the superior surface of a retained endotracheal tube, wherein the tube guiding surface of the inferior tube guiding member extends proximally of the tube guiding surface of the first tube guiding member. The tube guide may further comprise a second superior tube guiding member which has a tube guiding surface on an inferior side thereof for contacting and thereby guiding the superior surface of a retained endotracheal tube, wherein the second superior tube guiding member is proximal of the first superior tube guiding member and the tube guiding surfaces of the first and second superior tube guiding members are spaced apart, wherein the tube guiding surface of the second superior tube guiding member is spaced apart from and proximal of the proximal end of the tube guiding surface of the inferior tube guiding member, such that an endotracheal tube can be introduced into the tube guide between the proximal end of the tube guiding surface of the inferior tube guiding member and the distal end of the tube guiding surface of the superior tube contacting member at an angle to the length of the insertion section at the proximal end of the tube guiding surface of the inferior tube guiding member.

According to a fourth aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx, the tube guide comprising a plurality of tube guiding members having tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and a first superior tube guiding member at the distal end of the tube guide having a tube guiding surface on an inferior side thereof for contacting and thereby guiding the superior surface of a retained endotracheal tube, wherein the tube guide is arranged so that, for endotracheal tubes of a range of external diameters, a retained endotracheal tube will be continuously curved at least from where a retained endotracheal tube extends through a patient's teeth when the insertion section is inserted fully into a patient to the first superior tube guiding member.

As the tube guide is arranged to retain an endotracheal tube such that it is curved at least from where a retained endotracheal tube extends through a patient's teeth when the insertion section is inserted fully into a patient to the first superior tube guiding member, the tube will be easier to insert than would be the case if the endotracheal tube was retained in a generally J-shaped formation and the insertion section will be easier to insert than if the insertion section was arranged in a generally J-shaped formation.

The tube guide may be arranged to retain the endotracheal tube with a constant radius of curvature.

The tube guide may be arranged such that a retained endotracheal tube has a greater curvature between where it extends through a patient's teeth when the insertion section is inserted fully into a patient and the first superior tube guiding member than the curvature of the insertion section between where it extends through a patient's teeth when the insertion section is inserted fully into a patient and the first superior tube guiding member.

According to a fifth aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx and an elongate member, wherein the tube guide comprises a plurality of tube guiding members which extend laterally of the elongate member having tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and a first superior tube guiding member having a tube guiding surface on an inferior side thereof for contacting and thereby guiding the superior surface of a retained endotracheal tube, wherein, at at least one location along the length of the insertion section, the thickness of the elongate member is less than the thickness of the adjacent tube guide.

According to a sixth aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx and an elongate member, wherein the tube guide comprises a plurality of tube guiding members which extend laterally of the elongate member and have tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and a first superior tube guiding member having a tube guiding surface on an inferior side thereof for contacting and thereby guiding the superior surface of a retained endotracheal tube, wherein either or both (i) the inferior tube guiding member extends further in an inferior direction than the elongate member adjacent to the inferior tube guiding member or (ii) the superior tube guiding member extends further in a superior direction than the elongate member adjacent to the superior tube guiding member.

According to a seventh aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx, wherein the tube guide is adapted to retain endotracheal tubes with a range of external diameters within an operating range of endotracheal tube external diameters, under flexural tension.

Preferably, the tube guide comprises a plurality of tube guiding members having tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, a first superior tube guiding member having a tube guiding surface on an inferior side thereof for contacting and thereby guiding the superior surface of a retained endotracheal tube, and a second superior tube guiding member located proximally of the first superior tube guiding member and having a tube guiding surface on an inferior side thereof for contacting and thereby guiding the superior surface of a retained endotracheal tube, wherein the tube guiding surfaces of the first and second superior tube guiding members are spaced apart, with at least a portion of the tube guiding surface of the inferior tube guiding member being proximal of the proximal end of the tube guiding surface of the first superior tube guiding member and distal of the distal end of the tube guiding surface of the second superior tube guiding member, wherein the tube guiding members are arranged to retain endotracheal tubes with a range of external diameters within an operating range of endotracheal tube external diameters under flexural tension such that a retained endotracheal tube exerts a force in a superior direction on the first and second superior tube guiding members applying a force in an inferior direction and a force in an inferior direction on the inferior tube guiding member.

Preferably, the tube guide is arranged to that a retained endotracheal tube can be removed laterally from the tube guide. More preferably, the insertion section comprises an elongate member and the tube guiding members extend laterally from the elongate member.

According to an eighth aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx and an elongate member, wherein the tube guide comprises a plurality of tube guiding members which extend laterally of the elongate member and have tube guiding surfaces which are arranged to contact and thereby guide the inferior or superior surface of a retained endotracheal tube, the plurality of tube guiding members comprising at least an inferior tube guiding member having a tube guiding surface on a superior side thereof for contacting and thereby guiding the inferior surface of a retained endotracheal tube, and a first superior tube guiding member having a tube guiding surface on an inferior side thereof for contacting and thereby guiding the superior surface of a retained endotracheal tube, wherein there is at least one location, proximal of the first superior tube guiding member, where an endotracheal tube is retained in use laterally of the elongate member with the inferior and superior sides of the endotracheal tube being left exposed.

According to a ninth aspect of the present invention there is provided an elongate laryngoscope insertion section having a proximal end and a distal end for insertion into a patient's oral cavity in use, the insertion section comprising a tube guide for removably retaining an endotracheal tube and guiding a retained endotracheal tube towards a patient's larynx, wherein the insertion section and tube guide are arranged to leave the inferior or superior surface of a retained endotracheal tube exposed along at least 25% and preferably 50% or more preferably 75% of the length of the insertion section between the most proximal location where the insertion section contacts a retained endotracheal tube and the most distal location where the insertion section contacts a retained endotracheal tube.

Preferably, the inferior surface of a retained endotracheal tube is left exposed along at least 25% and preferably 50% or more preferably 75% of the length of the insertion section between the most proximal location where the insertion section contacts a retained endotracheal tube and the most distal location where the insertion section contacts a retained endotracheal tube.

Preferably, the superior surface of a retained endotracheal tube is left exposed along at least 25% and preferably 50% or more preferably 75% of the length of the insertion section between the most proximal location where the insertion section contacts a retained endotracheal tube and the most distal location where the insertion section contacts a retained endotracheal tube.

Preferably, both the inferior and superior surface of a retained endotracheal tube are left exposed along a continuous region of at least 5% or preferably at least 10% of the length of the insertion section between the most proximal location where the insertion section contacts a retained endotracheal tube and the most distal location where the insertion section contacts a retained endotracheal tube. Preferably, the continuous region is located close to the teeth of a patient of typical dimensions when the insertion section is inserted fully into a patient in use.

Preferably, the tube guide is arranged to enable a retained endotracheal tube to be removed laterally from the tube guide and a retained endotracheal tube is retained with its lateral side at least partially exposed along the entire length of the insertion section. Preferably, the insertion section comprises an elongate member, wherein the tube guide comprises a plurality of tube guiding members which extend laterally of the elongate member and have tube guiding surfaces which are arranged to contact and thereby guide the inferior or superior surface of a retained endotracheal tube, the plurality of tube guiding members comprising at least a first superior tube guiding member having a tube guiding surface on an inferior side thereof for contacting and thereby guiding the superior surface of a retained endotracheal tube and a second superior tube guiding member having a tube guiding surface on an inferior side thereof for contacting and thereby guiding the superior surface of a retained endotracheal tube, wherein the second superior tube guiding member is located proximally of the first superior tube guiding member and the tube guiding surfaces of the first and second superior tube guiding members are spaced apart, wherein the tube guiding surface of the second superior tube guiding member is the most proximal location where the insertion section contacts a retained endotracheal tube. The tube guiding surface of the first superior tube guiding member is preferably the most distal location where the insertion section contacts the superior side of a retained endotracheal tube and the tube guiding surface of the first superior tube guiding member may be the most distal location where the insertion section contacts a retained endotracheal tube.

Optional features discussed in relation to any of the first through ninth aspects of the invention are optional features of any of the first through ninth aspects of the invention. The invention also extends, in a tenth aspect, to a laryngoscope comprising a handle and an elongate insertion section according to any one of the first nine aspects of the invention.

The insertion section may be fixedly attached to the handle. Alternatively, the laryngoscope may comprise a body which comprises the handle and the elongate insertion section may be detachably retainable on the body. The insertion section may comprise an elongate member having a bore therein and the body may comprise an insertion section supporting member which extends into and support the insertion section. Further optional and preferred features of the insertion section supporting member, elongate member and bore correspond to those discussed above in relation to the first nine aspects of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
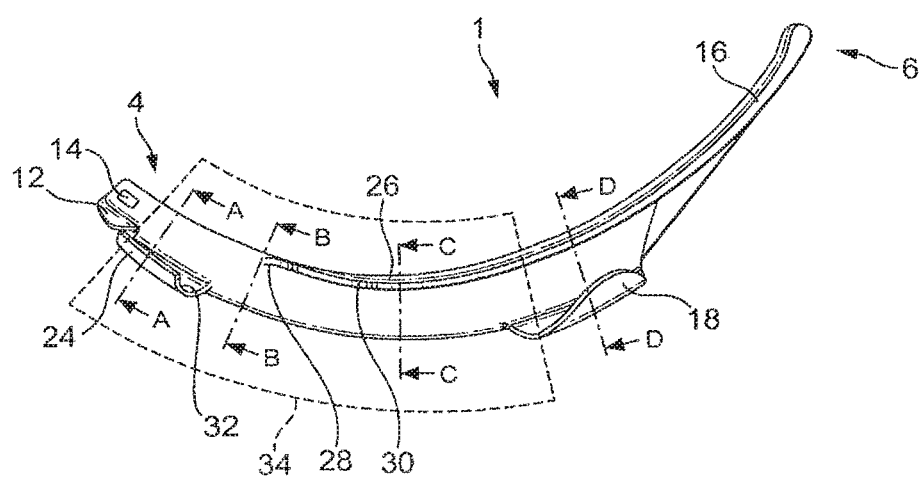
FIG. 1 is an orthogonal view from a lateral position of a laryngoscope insertion section according to the present invention.
Figure 2:
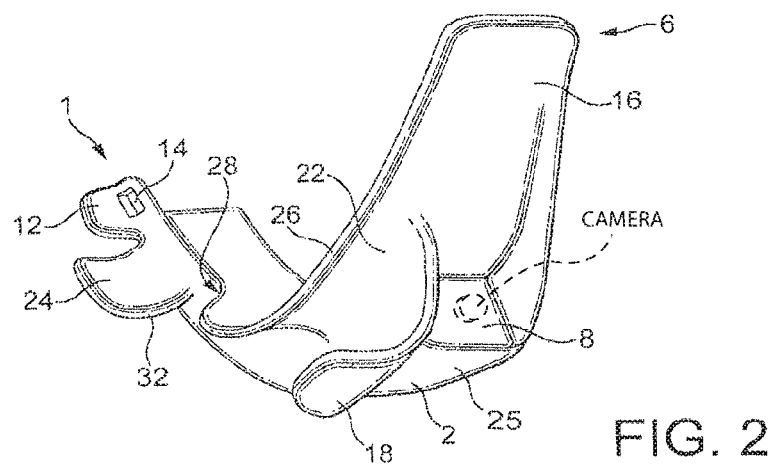
FIGS. 2 to 4 are perspective views from a range of orientations of the laryngoscope insertion section of FIG. 1.
Figure 3:
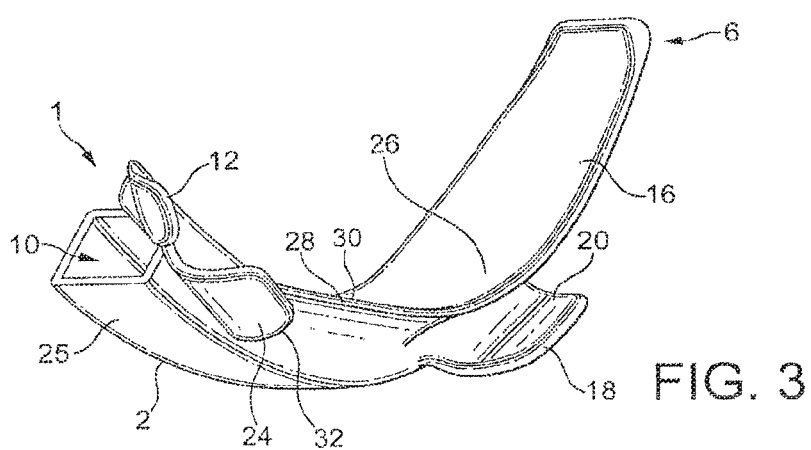
Figure 4:
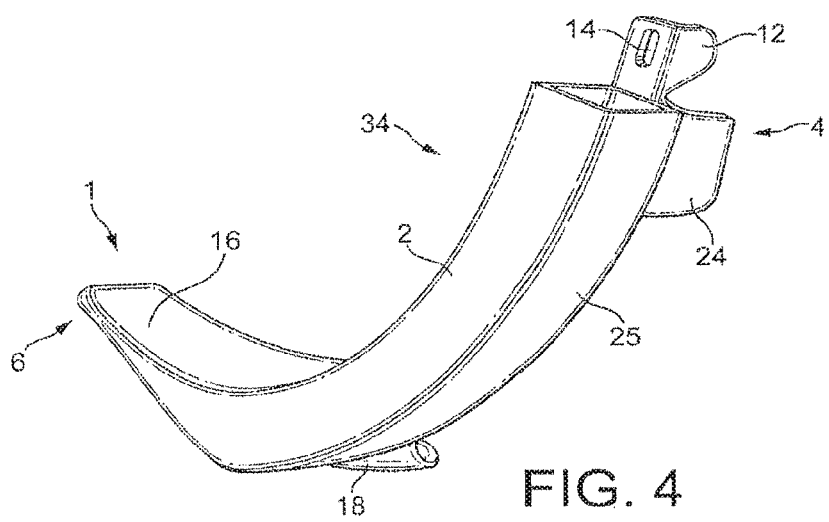

With reference to FIGS. 1 to 5, a laryngoscope insertion section for use with adult humans, shown generally as 1, comprises an elongate member 2 which extends from the proximal end of the insertion section 4 but does not extend as far as the distal end of the insertion section 6. The elongate member has a light-permeable viewing port 8 at its distal end. An elongate bore 10 extends along the elongate member from the proximal end of the elongate member for receiving and retaining an insertion section retaining protrusion of a laryngoscope and covering the insertion section retaining protrusion to protect it from bodily fluids in use. A retaining portion 12, which includes a fixing aperture 14 for engaging with a corresponding protrusion on an insertion section supporting member of a laryngoscope, facilitates the removable attachment of the insertion section to a laryngoscope. The insertion section may be used with a laryngoscope including a insertion section retaining member with a video camera and light source which is included in the insertion section retaining member, so that light from the light source can illuminate a patient's trachea and the surrounding region and the video camera can relay images of the patient's trachea and the surrounding region to a display. A broad protrusion 16 extends from the end of the elongate member, which functions as a blade for contacting and typically lifting a patient's anatomy in use to provide clear access to the larynx.

A tube guide extends laterally of the elongate member. The tube guide comprises a distal superior tube guiding member 18, located towards the distal end of the insertion section, which extends from the superior side of the elongate member and functions as the first superior tube guiding member. The inferior surface of the distal superior tube guiding member includes a tube guiding surface 20 which is arranged to contact and thereby guide the superior surface of a retained endotracheal tube. A lateral edge 22 of the elongate member does not function as the tube guiding surface as, although it may contact an endotracheal tube in use, it does not contact and thereby guide the superior surface of a retained endotracheal tube.

The tube guide also comprises a proximal superior tube guiding member 24, located towards the proximal end of the insertion section, which extends laterally from the elongate member and functions as the second superior tube guiding member. The inferior surface of the proximal superior tube guiding member also includes a tube guiding surface which is arranged to contact and thereby guide the superior surface of a retained endotracheal tube.

The tube guiding surfaces of the proximal and distal superior tube guiding members are generally incurvate. The proximal and superior tube guiding members are of generally even thickness and extend laterally and superiorly from the elongate member, from a location on the lateral side of the elongate member which is near to but not level with the superior surface 25 of the elongate member. They extend superiorly to the superior surface of the elongate member, curve over a retained endotracheal tube in use and then curve laterally and inferiorly to extend over and guide the superior surface of a retained endotracheal tube. The tube guiding surface of the proximal superior tube guiding member extends superiorly relative to the insertion section towards its distal end. The tube guiding surface of the distal superior tube guiding member extends inferiorly relative to the insertion section towards its distal end. This arrangement facilitates the retention of an endotracheal tube with a greater curvature than the insertion section.

An inferior tube guiding member 26 extends from a location which is distal of the proximal superior tube guiding member towards the distal end of the insertion section. The inferior tube guiding member comprises a tube guiding surface which is arranged to contact and thereby guide the inferior surface of a retained endotracheal tube. The inferior tube guiding member tapers at a proximal end and so it also comprises an inferior surface portion 28 which does not function as a tube guiding surface because it does not contact and thereby guide the inferior surface of a retained endotracheal tube in use. The tube guiding surfaces of the inferior tube guiding member is also generally incurvate. The inferior tube guiding member is of generally even thickness and extends laterally and inferiorly from the elongate member, from a location on the lateral edge of the elongate member which is near to but not level with the inferior surface 25 of the elongate member. The inferior tube guiding member extends inferiorly to the inferior surface of the elongate member, curves over a retained endotracheal tube in use and then curves laterally and superiorly to extend under and guide the inferior surface of a retained endotracheal tube.

The tube guide is arranged to leave the inferior and superior surfaces of a retained endotracheal tube exposed along a majority of the length of the insertion section between the most proximal and most distal locations where the endotracheal tube contacts a retained endotracheal tube. In an insertion section for use with adult humans, the length of the proximal superior tube guiding member, along its most superior region, may be approximately 22 mm and the length of the distal superior tube guiding member, along its most superior region, may be approximately 15 mm. The distance between the distal end of the proximal superior tube guiding member and the proximal end of the distal superior tube guiding member, following the curve of the insertion section, between the most superior regions of the proximal and distal superior tube guiding members, may be approximately 68 mm, or 65 mm in a direct line. The distance between the proximal end of the inferior tube guiding member and the distal end of the proximal superior tube guiding member may be approximately 25 mm and the inferior tube guiding member may extend approximately 45 mm proximally of the proximal end of the distal superior tube guiding member.

The inferior tube guiding member and the distal superior tube guiding member are arranged to guide a retained endotracheal tube 29 towards a patients' trachea in use. The tube guiding surfaces of the proximal and distal superior tube guiding members are spaced apart because the proximal and distal superior tube guiding members are spaced apart. The superior surface of a retained endotracheal tube is exposed between the tube guiding surfaces of the proximal and distal superior tube guiding members. The inferior tube guiding member extends proximally of the distal superior tube guiding member and so there is a region where a retained endotracheal tube is guided on its inferior side but not its superior side. The proximal end 30 of the tube guiding surface inferior tube guiding member is spaced apart from the distal end 32 of the proximal superior tube guiding member, by a sufficient distance to enable a 12.3 mm external diameter endotracheal tube (being the upper end of an operating range of endotracheal tube sizes) to be introduced at an angle to the centre line of the insertion section.

Figure 5:
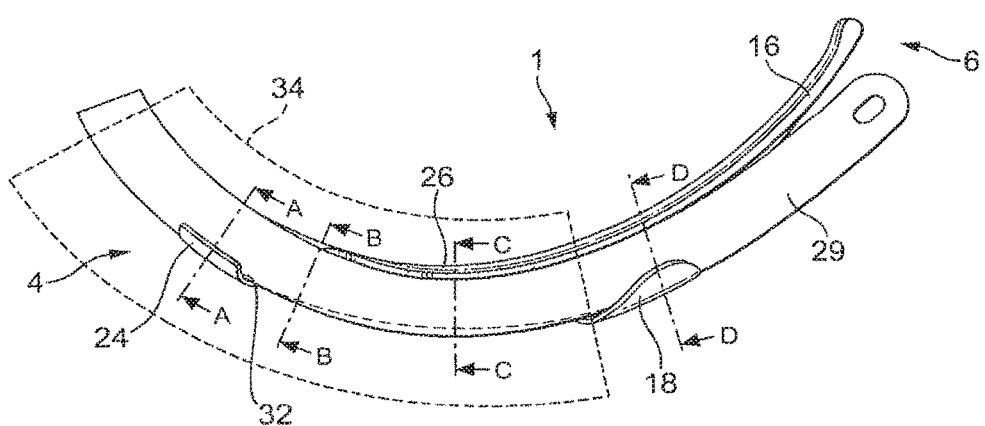
FIG. 5 is an orthogonal view from a lateral position of the laryngoscope insertion section of FIG. 1 detachably retaining an endotracheal tube with a diameter at the upper end of an operating range of endotracheal tube sizes.
Figure 6:
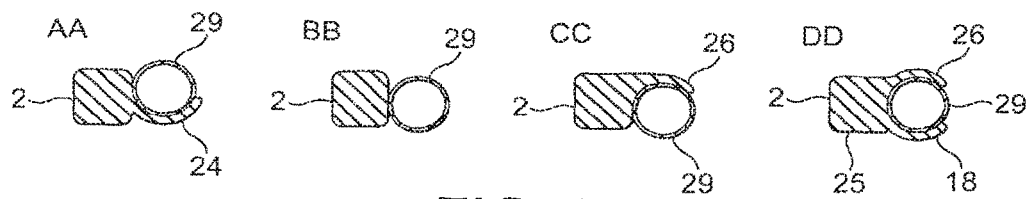
FIG. 6 is a series of cross-sections through the insertion section and retained endotracheal tube of FIG. 5 along cut lines A-A, B-B, C-C and D-D.

FIG. 6 comprises a series of cross-sections through the insertion section of FIG. 5 along cut lines A-A, B-B, C-C and D-D. Note that in this arrangement the superior surface of the proximal superior tube guiding member is substantially in line with the superior surface of the elongate member (A-A) and the endotracheal tube (which has a diameter of 12.3 mm) has a superior surface which extends superiorly of the superior surface of the adjacent elongate member (C-C). Level with the distal superior tube guiding member (D-D), the inferior surface of the inferior tube guiding member extends further in an inferior direction than the inferior surface of the elongate member.

Furthermore, level with the distal superior tube guiding member, the superior surface of the distal superior tube guiding member extends further in a superior direction than the superior surface of the elongate member.

Figure 7:
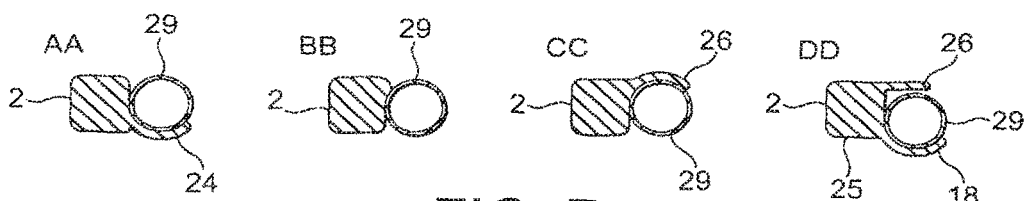
FIG. 7 is a series of cross-sections through an alternative insertion section and retained endotracheal tube along cut lines equivalent to A-A, B-B, C-C and D-D of FIG. 1.

FIG. 7 comprises a series of cross-sections through an alternative insertion section along cut lines which are equivalent to A-A, B-B$_1$C-C and D-D. In this embodiment, the inferior tube guiding member is not incurvate but has an inferior surface which is level with the inferior surface of the elongate member and the superior surface of the distal superior tube guiding member extends superiorly of the superior surface of the elongate member. The superior surface of the proximal superior tube guiding member extends further in a superior direction than the superior surface of the elongate member (A-A). At the proximal end of the inferior tube guiding member, the inferior surface of the a retained endotracheal tube with 12.3 mm diameter extends further in an inferior direction than the inferior surface of the elongate member. Further along the inferior tube guiding member, the inferior surface of the inferior tube guiding member extends inferiorly of the inferior surface of the elongate member.

Figure 8:
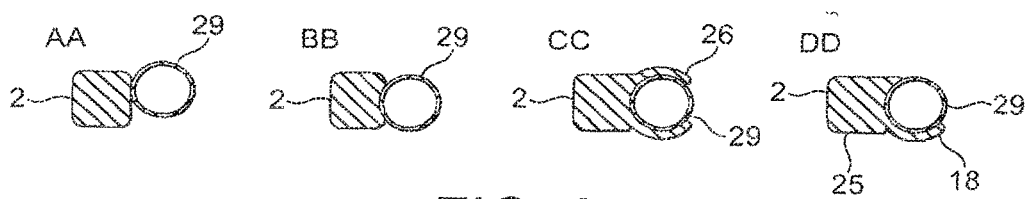
FIG. 8 is a series of cross-sections through a further insertion section and retained endotracheal tube along cut lines equivalent to A-A, B-B, C-C and D-D of FIG. 1.

FIG. 8 comprises a series of cross-sections through an alternative insertion section along cut lines which are equivalent to A-A, B-B, C-C and D-D. In this embodiment, no proximal superior tube guiding member is provided (A-A). The inferior tube guiding member extends further inferiorly than in the previous embodiments to facilitate smooth insertion of the tube when it is pushed along its length by an intubator (C-C). The lateral surface of the elongate member comprises a slight elongate groove (B-B) to better retain an endotracheal tube within the tube guide. Level with the proximal half of the distal superior tube guiding member (C-C), the inferior surface of the inferior tube guiding member extends further in an inferior direction than the inferior surface of the elongate member. Furthermore, level with the proximal half distal superior tube guiding member, the superior surface of the distal superior tube guiding member extends further in a superior direction than the superior surface of the elongate member. The superior tube guiding member extends distally of the inferior tube guiding member as illustrated at cross-section D-D.

The various cross-sections illustrated in FIGS. 6 to 8 may be combined in any combination to form a range of insertion sections.

Figure 9:
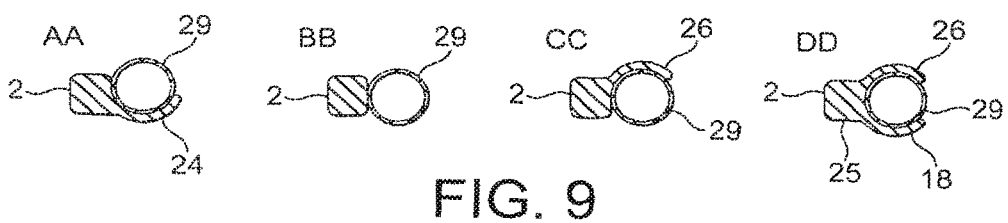
FIG. 9 is a series of cross-sections through a still further insertion section and retained endotracheal tube along cut lines equivalent to A-A, B-B, C-C and D-D of FIG. 1.
Figure 10:
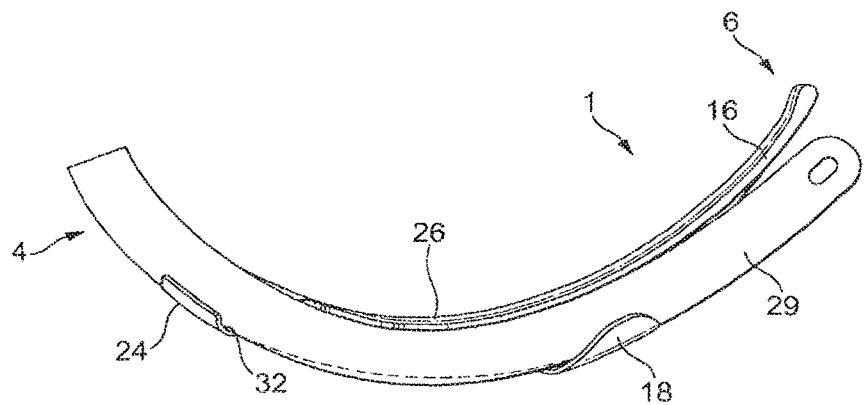
FIG. 10 is an orthogonal view from a lateral position of the laryngoscope insertion section of FIG. 1 detachably retaining an endotracheal tube with a diameter at the upper end of an operating range of endotracheal tube sizes.
Figure 11:
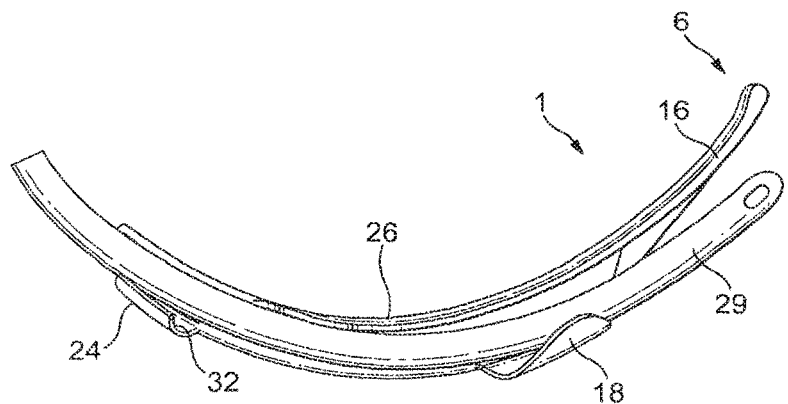
FIG. 11 is an orthogonal view from a lateral position of the laryngoscope insertion section of FIG. 1 detachably retaining an endotracheal tube with a diameter at the lower end of an operating range of endotracheal tube sizes.

FIG. 9 comprises a series of cross-sections through a still further alternative insertion section along cut lines which are equivalent to A-A, B-B, C-C and D-D. In this embodiment, which has especially reduced bulk, the elongate member is narrower and the tube guiding members extend significantly further in an inferior or superior direction, as appropriate, than the adjacent corresponding surface of the elongate member. At cross section B-B, the retained 12.3 mm endotracheal tube extends superiorly and inferiorly of the superior and inferior surfaces of the elongate member respectively. Accordingly, there is a region of insertion section, between the proximal distal superior tube guiding member and the proximal end of the tube guiding surface of the inferior tube guiding member where the thickness of the insertion section is less than the thickness of the adjacent 12.3 mm endotracheal tube. At this location, and proximal of the proximal superior tube guiding member the thickness of the elongate member may be less than 8 mm and perhaps as thin as 3 mm or 4 mm.

The insertion section is typically moulded in one piece from a transparent plastics material and supplied sterilised within a sealed package.

In use, the insertion section is detachably mounted on an elongate insertion section supporting member (not shown) which fits snugly within the bore. The elongate insertion section supporting member is typically attached to the handle of a laryngoscope body. A video camera, functioning as imaging apparatus and a light emitting diode, functioning as light source, are located on the distal tip of the elongate insertion section supporting member, such that they are adjacent to the window in use. Electric wires run down the length of the elongate insertion section supporting member which supply power to the video camera and light source.

The elongate strengthening section is typically fabricated from steel or another rigid material. As well as supporting the video camera and light source and enclosing the electrical connections to the video camera and light source, the elongate strengthening section functions to provide support the insertion section, enabling it to be thinner than would otherwise be the case.

Once the insertion section has been attached to a laryngoscope body, an endotracheal tube within an operating range of endotracheal tube sizes which can be used reliably with the insertion section is inserted into the tube guide, in contact with the tube guiding surfaces of the inferior tube guiding member and the proximal and distal tube guiding members. For an insertion section for use in the intubation of human adults, a suitable operating range of external tube diameters would be 8 mm to 12.3 mm.

The laryngoscope with insertion section is then introduced into a patient, the blade is used to contact, and perhaps lift, the patient's anatomy to obtain clear access to the larynx. The light emitting diode illuminates the patient's laryngeal area whilst images from the video camera are relayed to a display which might be an integral part of the laryngoscope or may be separate to the laryngoscope. The laryngoscope is inserted fully into a patient, i.e. to the point where an anaesthetist would consider it to be optimally aligned for the introduction of an endotracheal tube. The endotracheal tube is then advanced forward through the insertion section into the patient's larynx. Once the tube has been successfully inserted, it can be detached laterally from the insertion section and separated from the insertion section in situ. The insertion section can then be removed and the endotracheal tube left in place.

Note that endotracheal tubes will be retained within the tube guide under flexural tension. Although endotracheal tubes typically have an inherent curvature, the retained endotracheal tubes will be subject to bending forces in the inferior direction at both the proximal and distal superior tube guiding member and a force in the superior direction at at least a portion of the inferior tube guiding member. Endotracheal tubes are resilient and so they exert a force 42 in a superior direction on at least the distal ends of the proximal and distal superior tube guiding members and a further force 44 in an inferior direction on at least a region of (typically towards or at the proximal end) the inferior tube guiding member. This improves the grip of the tube guiding members on a retained endotracheal tube enabling the tube guiding members to have lower profiles and to extend less far around retained endotracheal tubes than would otherwise be the case, facilitating the provision of a reliable laterally opening tube guide.

In practice, retained endotracheal tubes of at least some diameters (typically at the upper end of the operating range of endotracheal tube sizes) will typically contact the tube guiding surface of the proximal and distal superior tube guiding members only at the distal ends of these tube guiding members, due to the curved path of the retained tube, whilst the endotracheal tube is at rest within the guide. Other tube guiding surfaces of the proximal and distal superior tube guiding members are relevant during the stage of inserting an endotracheal tube into the tube guide, although they could conceivably be omitted. Similarly, such endotracheal tubes will typically only contact the tube guiding surface of the inferior tube guiding member towards the proximal end of the tube guiding surface, again due to the curved path of the retained endotracheal tube. This arrangement, in which the endotracheal tubes only contact a limited region of some or all of the tube guiding members reduces friction when the endotracheal tube is advanced into a patient's trachea.

The insertion section has a number of key advantages which result from features of the design. Firstly, the insertion section is adapted to minimise the risk of damaging a patient's teeth and to facilitate the manoeuvrability of the insertion section in the region of a patient's teeth as there is a substantial narrow region 34, functioning as the first region, where the thickness of the insertion section is less than the external diameter of the largest size of endotracheal tube in an operating range of endotracheal tubes (12.3 mm in this example) plus the thickness of the inferior tube contacting member where it contacts the inferior surface of a retained endotracheal tube (at least 0.75 mm and typically 1.5 mm) plus the thickness of the distal superior tube contacting member where it contacts the superior surface of a retained endotracheal tube (at least 0.75 mm and typically 1.5 mm). Although the narrow region extends along the majority of the length of the insertion section in this example, it would be useful to provide a narrow section with a thickness which is less than the abovementioned thickness, even if it only extended along a short portion of the insertion section, such as along a length of 2 cm, 1 cm or even 0.5 cm of the insertion section, close to a patient's teeth when the insertion section is fully inserted into a patient of typical dimensions.

One feature which enables the thickness of the tube guide to remain less than the said thickness (15.3 mm in the present example) proximal of the distal superior tube contacting member is the arrangement in which the tube guiding surfaces of the proximal and distal superior tube contacting members are spaced apart, leaving the superior surface of a retained endotracheal tube exposed. The presence of an inferior tube guiding member and a distal superior tube guiding member is sufficient to guide the tube. However, the arrangement in which the inferior tube guiding member extends proximally of the tube guiding surface of the distal superior tube guiding member and there is a region where the superior surface of a retained tube is left exposed opposite a first region of tube guiding surface of the inferior tube guiding member, has the benefit that a retained tube can be accurately guided by the inferior tube guiding member but the bulk of the insertion section is reduced by the omission of the a tube guiding member opposite the said region of the inferior tube guiding member.

Similarly, as no tube guiding surface is provided opposite the tube guiding surface of the proximal superior tube guiding member, the thickness of the tube guide remains less than the said thickness (15.3 mm in the present example) close to a patient's teeth in use. There is a region between the distal end of the tube guiding surface of the proximal superior tube guiding member and the proximal end of the tube guiding surface of the inferior tube guiding member where a retained endotracheal tube is exposed on both its inferior and superior surfaces. This is advantageous firstly in that the overall bulk of the insertion section has been reduced by omitting tube guiding members in this region. This enables the inferior tube guiding member and a projection of the superior tube guiding member to be spaced apart by less than the external diameter of an endotracheal tube at the top end of an operating range of tube sizes (12.3 mm external diameter in the present example).

Figure 12:
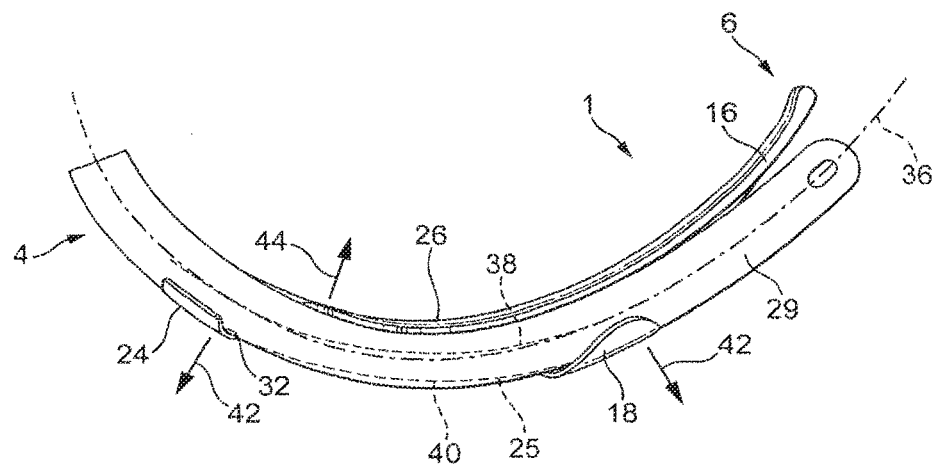
FIG. 12 corresponds to FIG. 10 including indications of the centre lines of the retained endotracheal tube and the insertion section.

Furthermore, this arrangement facilitates the introduction of an endotracheal tube at the top end of an operating range of tube sizes at an angle to the length of the insertion section. This is best illustrated in FIG. 12 where it will be seen that the centre line 36 of the retained 12.3 mm endotracheal tube has a greater radius of curvature than the centre line of the insertion section 38 and, indeed, the most superior point on the retained endotracheal tube is superior of the superior surface of the insertion section. Thus, the endotracheal tube extends into the volume which would be occupied by a superior tube guiding member if the superior tube guiding member had extended to the proximal end of the inferior tube guiding member. Accordingly, the insertion section is thinner from the proximal superior tube guiding member to the distal superior tube guiding member than would have been the case if the tube guide covered both the inferior and superior surface of a retained endotracheal tube along this length. An endotracheal tube at the bottom end of the operating range of endotracheal tube sizes might alternatively have a smaller radius of curvature and may not contact the inferior tube guiding member.

It is also notable that the thickness of the tube guide is greater level with the distal superior tube guiding member than the thickness of the adjacent elongate member. Furthermore, the superior surface of the distal superior tube guiding member extends further in a superior direction than the superior surface of the adjacent elongate member and the inferior surface of the inferior tube guiding member extends further in an inferior direction than the inferior surface of the elongate member adjacent to the inferior tube guiding member. Accordingly, the overall bulk of the insertion section is less than would be the case if the inferior and superior surfaces of the tube guiding members extended level with the inferior and superior surfaces respectively of the elongate member, along the entire length of the insertion section. This substantially reduces the overall bulk of the insertion section, facilitating rapid intubation.

The maintenance of a retained endotracheal tube in a curved path is facilitated by the provision of a distal superior tube contacting member which has an inferior tube guiding surface which is at an angle to the centre line of the insertion section, such that it extends inferiorly towards its distal end. Similarly, the proximal superior tube contacting member has an inferior tube guiding surface which is at an angle to the centre line of the insertion section, such that it extends superiorly towards its distal end.

In some embodiments, illustrated in FIG. 7, the superior surface of the proximal superior tube guiding member extends further in a superior direction than the superior surface of the elongate member adjacent to the proximal superior tube guiding member which reduces the bulk of the insertion section in the region of a patient's teeth when the insertion section is fully inserted into a patient's oral cavity.

In some embodiments, illustrated in FIG. 8, the proximal superior tube guiding member is entirely omitted. The tube guiding surface of the inferior tube guiding member does not extend to the proximal end of the insertion section. This reduces bulk further and is facilitated by the provision of an inferior tube guiding member having a tube guiding surface which does extend proximally of the proximal end of the tube guiding surface of the distal superior tube guiding member. In some embodiments, the tube guiding surface of the distal superior tube guiding member is entirely distal of the portion of the insertion section (which is typically the most curved) which extend around the base of a patient's tongue in use. However, in the embodiment illustrated in FIG. 8, the tube guiding surface of the distal superior tube contacting member does extend to the portion of the insertion section which extends around the base of a patient's tongue in use.

In the embodiment of FIG. 9, the thickness of the elongate member is significantly reduced, to less than the external diameter of the largest endotracheal tube in the operating range of endotracheal tubes, to further reduce the overall bulk of the insertion section.

A further benefit of arranging the tube guide such that a retained endotracheal tube remains curved between the proximal end of the insertion section and the distal superior tube guiding member is that, in contrast to J-shaped insertion sections with tube guides, the insertion section can be more naturally introduced into a patient's oral cavity along a curved path. In contrast, J-shaped insertion sections require to be tilted backwards and forward as they inserted in a multi-stage process. Furthermore less force would be required to advance the retained tube into a patient's trachea than with a J-shaped tube guide, where significant force would be exerted on the tube guide where the straight portion began to curve. Endotracheal tubes are typically slightly curved and this arrangement facilitates convenient use of slightly curved endotracheal tubes.

As a result of the design features which reduce the overall bulk of the insertion section, the insertion section can be made of a size to work with larger diameter endotracheal tubes. For example, an insertion section which can be easily used for rapid insertion of a tube in difficult intubation situations can be provided which can be used with endotracheal tubes with a diameter of up to 12.3 mm.

Alternative insertion sections may be provided for use with infant humans, or specific animals or groups of animals, such as horses. In this case, the insertion section may be scaled proportionately. The length, width and thickness of the insertion section as a whole are typically scaled proportionately. Nevertheless, some dimensions, such as the thickness of the tube guiding members, may not be scaled proportionately.

It will be seen that the tube guide has been arranged to retain an endotracheal tube laterally of the elongate member, fitting better with the general shape of a patient's oral cavity than a tube guide which retain an endotracheal tube inferiorly or superiorly of the insertion section.

Although the illustrated embodiments show proximal and distal superior tube guiding members which finish abruptly so that the tube guiding surfaces of the proximal and distal superior tube guiding members terminate at the proximal and distal ends of each superior tube guiding member, either or both of the proximal and distal superior tube guiding members could instead taper and include portions which did not function as tube guiding surfaces which contact and thereby guide the superior surface of a retained endotracheal tube. For example, a lip extending from the elongate member may connect the proximal and distal superior tube guiding members, but not affect the function of the invention because the lip does not constitute a tube guiding surface within the meaning of the present invention.

Although the invention has been illustrated using a detachably retainable insertion section portion, the insertion section may alternatively be an integral part of a laryngoscope. Further modifications and variations may be made within the scope of the invention herein disclosed.

What is claimed is:

1. A laryngoscope blade configured for insertion into a patient's oral cavity and comprising:
   an elongate member extending between a proximal terminus and a distal terminus of the laryngoscope blade, wherein the elongate member forms a cavity extending along at least a portion of the elongate member from an opening at the proximal terminus and terminating before the distal terminus of the laryngoscope blade;
   a superior tube guide positioned adjacent to and laterally extending from a superior surface of the elongate member, wherein the superior tube guide is configured to retain and to guide an endotracheal tube toward the patient's oral cavity, and wherein the superior tube guide comprises an inferior guiding surface configured to be in contact with at least a portion of a superior outer wall of a retained endotracheal tube when in use, and wherein at least a portion of the superior tube guide is positioned adjacent to the proximal terminus of the laryngoscope blade; and
   an inferior tube guide positioned adjacent to and laterally extending from an inferior surface of the elongate member, wherein the inferior tube guide comprises a superior guiding surface configured to contact at least a portion of an inferior outer wall of the retained endotracheal tube, and wherein the cavity is disposed between the superior surface and the inferior surface of the elongate member.

2. The laryngoscope blade of claim 1, wherein at least a portion of the inferior guiding surface is curved downward toward the inferior tube guide and at least a portion of the superior guiding surface is curved upward toward the superior tube guide.

3. The laryngoscope blade of claim 1, wherein the superior tube guide comprises a first guiding member positioned adjacent to the proximal end of the laryngoscope blade and a second guiding member spaced apart from and distal to the first guiding member.

4. The laryngoscope blade of claim 3, wherein the inferior tube guide is positioned distal to the first guiding member.

5. The laryngoscope blade of claim 3, wherein the second guiding member is spaced apart from the first guiding member such that the inferior guiding surface is non-continuous between the first guiding member and the second guiding member.

6. The laryngoscope blade of claim 1, wherein the superior tube guide comprises a first guiding member having a first proximal end and a first distal end and a second guiding member having a second proximal end and a second distal end, wherein the second proximal end is spaced apart from the first distal end such that, when the endotracheal tube is retained, a first region of the retrained endotracheal tube is in contact with the first guiding member of the superior tube guide and not the inferior tube guide, a second region of the retrained endotracheal tube is in contact with the second guiding member of the superior tube guide and the inferior tube guide, and a third region the retained endotracheal tube between the first region and the second region is in contact with the inferior tube guide and not the superior tube guide.

7. The laryngoscope blade of claim 6, wherein the inferior tube guide is in contact with a portion of the inferior outer wall of the retained endotracheal tube in the third region.

8. The laryngoscope blade of claim 1, comprising a protrusion extending away from the elongate member and toward the distal end of the laryngoscope blade, wherein at least a portion of the protrusion is configured to contact a patient's tissue when the laryngoscope blade is inserted into the patient's oral cavity.

9. The laryngoscope blade of claim 1, comprising a retaining portion adjacent to the opening and extending away from the proximal terminus, wherein the retaining portion comprises an aperture configured to be removably coupled to a coupling feature disposed on a handle of a laryngoscope.

10. The laryngoscope blade of claim 1, wherein the cavity terminates in a lens.

11. A laryngoscope blade configured for insertion into a patient's oral cavity and comprising:
    a superior tube guide laterally extending from a superior surface of the laryngoscope blade, wherein the superior tube guide comprise a first superior guiding member having a first inferior guiding surface and a second superior guiding member having a second inferior guiding surface, wherein the first and second superior guiding members are configured to retain and to guide an endotracheal tube toward the patient's oral cavity, and wherein the first superior guiding member is positioned adjacent to a proximal terminus of the laryngoscope blade such that a proximal end of the first superior guiding member is aligned with the proximal terminus of the laryngoscope blade; and
    an inferior tube guide laterally extending from an inferior surface of the laryngoscope blade and positioned distal to the first superior guiding member.

12. The laryngoscope blade of claim 11, wherein the first superior guiding member, the second superior guiding member, and the inferior tube guide are arranged along the laryngoscope blade such that a first region of the retained endotracheal tube is in contact with the first superior guiding member and not the second superior guiding member and the inferior guiding member, a second region of the retained endotracheal tube is in contact with the inferior tube guide and not the superior tube guide, and a third region of the endotracheal tube that is distal to the first and second regions is in contact with both the second superior guiding member and the inferior tube guide and not the first superior guiding member.

13. The laryngoscope blade of claim 11, wherein the inferior tube guide comprises a superior guiding surface configured to contact at least a portion of the retained endotracheal tube in a region between the first superior guiding member and the second superior guiding member.

14. The laryngoscope blade of claim 13, wherein the first inferior guiding surface and the second inferior guiding surface are curved downward toward the inferior tube guide, and the superior guiding surface is curved upward toward the superior tube guide.

15. The laryngoscope blade of claim 11, comprising an elongate member forming a cavity extending along at least a portion of the laryngoscope blade, wherein the cavity is disposed between the superior surface and the inferior surface of the laryngoscope blade, and wherein the elongate member comprises an opening at the proximal terminus and terminates in a lens proximal to a distal end of the laryngoscope blade.

16. A laryngoscope, comprising:
    a handle;
    a blade removably coupled to and extending away from the handle, wherein the blade comprises:

an elongate member forming a cavity extending along at least a portion of the elongate member from an opening at a proximal terminus of the blade and terminating before a distal terminus of the blade;

at least one superior guiding member laterally extending from a superior surface of the blade and that forms a curved inferior guiding surface, wherein the at least one superior guiding member is configured to retain and to guide a superior outer wall of an endotracheal tube toward a patient's oral cavity, and wherein at least a portion of the at least one superior guiding member is positioned adjacent to the proximal terminus of the laryngoscope blade; and an inferior tube guide laterally extending from an inferior surface of the blade and positioned distal to at least one superior guiding member, wherein the inferior tube guide comprises a superior guiding surface configured to retain and to guide an inferior outer surface of the endotracheal tube toward the patient's oral cavity, and wherein the cavity is disposed between the superior surface and the inferior surface.

17. The laryngoscope of claim 16, wherein the curved inferior guiding surface is curved toward the inferior tube guide.

18. The laryngoscope of claim 16, wherein the superior guiding surface of the inferior guiding member extends to the distal end of the blade.

19. The laryngoscope of claim 16, wherein a distance between an edge of the superior guiding surface and an edge of the curved inferior guiding surface is constant at least along a portion of the blade.

20. The laryngoscope of claim 16, wherein the blade comprises a retaining portion adjacent to the opening and extending away from the proximal terminus, wherein the retaining portion comprises an aperture configured to be removably coupled to a coupling feature disposed on the handle.

* * * * *